US012233148B2

United States Patent
Arora et al.

(10) Patent No.: US 12,233,148 B2
(45) Date of Patent: Feb. 25, 2025

(54) COMPOSITIONS CONTAINING POLYMERS AND AMINOSILICONE FOR CONDITIONING AND STYLING HAIR

(71) Applicant: L'OREAL, Paris (FR)

(72) Inventors: Shilpa Arora, South Plainfield, NJ (US); Lisa Chuyin Ye-Tse, Brooklyn, NY (US); Marie Huynh, Monmouth Junction, NJ (US); Azizah Khader Suleiman, Paterson, NJ (US); Anand Ramchandra Mahadeshwar, Mumbai (IN)

(73) Assignee: L'OREAL, Paris (FR)

( * ) Notice: Subject to any disclaimer, the term of this patent is extended or adjusted under 35 U.S.C. 154(b) by 351 days.

(21) Appl. No.: 16/428,867

(22) Filed: May 31, 2019

(65) Prior Publication Data
US 2020/0375869 A1   Dec. 3, 2020

(51) Int. Cl.
| | |
|---|---|
| *A61K 8/73* | (2006.01) |
| *A45D 7/04* | (2006.01) |
| *A61K 8/34* | (2006.01) |
| *A61K 8/60* | (2006.01) |
| *A61K 8/81* | (2006.01) |
| *A61K 8/891* | (2006.01) |
| *A61K 8/898* | (2006.01) |
| *A61Q 5/06* | (2006.01) |
| *A61Q 5/12* | (2006.01) |

(52) U.S. Cl.
CPC ............ *A61K 8/73* (2013.01); *A45D 7/04* (2013.01); *A61K 8/342* (2013.01); *A61K 8/602* (2013.01); *A61K 8/731* (2013.01); *A61K 8/732* (2013.01); *A61K 8/737* (2013.01); *A61K 8/8111* (2013.01); *A61K 8/8158* (2013.01); *A61K 8/891* (2013.01); *A61K 8/898* (2013.01); *A61Q 5/06* (2013.01); *A61Q 5/12* (2013.01)

(58) Field of Classification Search
None
See application file for complete search history.

(56) References Cited

U.S. PATENT DOCUMENTS

| | | | | |
|---|---|---|---|---|
| 5,827,510 A | * | 10/1998 | Mesquitta | A61Q 7/00 424/74 |
| 5,972,322 A | * | 10/1999 | Rath | A61K 8/31 424/70.11 |
| 6,358,502 B1 | | 3/2002 | Tanabe et al. | |
| 6,548,051 B2 | * | 4/2003 | Garnier | A61K 8/025 424/401 |
| 7,481,845 B2 | * | 1/2009 | De La Mettrie | A61K 8/02 132/202 |
| 7,928,027 B2 | * | 4/2011 | Mori | C03C 3/068 501/78 |
| 7,928,087 B2 | * | 4/2011 | Fack | A61K 8/73 514/54 |
| 2007/0248558 A1 | * | 10/2007 | Stein | A61K 8/068 424/70.13 |
| 2014/0341831 A1 | * | 11/2014 | Mahmud | A61K 8/347 424/70.17 |
| 2014/0349902 A1 | * | 11/2014 | Allef | A61K 8/361 510/119 |
| 2016/0279048 A1 | * | 9/2016 | Jayaswal | A61Q 5/02 |
| 2019/0160000 A1 | | 5/2019 | Herrlein et al. | |

FOREIGN PATENT DOCUMENTS

| | | | |
|---|---|---|---|
| EP | 2214633 B1 | 8/2011 | |
| EP | 3295820 B1 | 5/2019 | |
| JP | 2013-63959 A * | 4/2013 | ............ A61Q 5/12 |
| WO | 2014111578 A1 | 7/2014 | |

OTHER PUBLICATIONS

Momentive Marketing Bulletin, Silsoft CLX-E, Conditioning Agent (Year: 2015).*

* cited by examiner

*Primary Examiner* — Nicole P Babson
(74) *Attorney, Agent, or Firm* — McNees Wallace & Nurick LLC

(57) ABSTRACT

A hair treatment composition in a anionic, nonionic or amphoteric system includes water and a novel association of polysaccharide, such as inulin, and a film-forming polymer, such as polysilicone-29. The composition may include one or more additional components selected from polymers such as anionic polymers and nonionic polymers, amphoteric surfactants, or fatty compounds, embodied to deliver one or more of smoothing, straightening and curling/curl defining style features to achieve a particular straight or curly style with frizz control, softness and manageability.

21 Claims, No Drawings

COMPOSITIONS CONTAINING POLYMERS AND AMINOSILICONE FOR CONDITIONING AND STYLING HAIR

TECHNICAL FIELD

The instant disclosure relates to compositions, kits, and methods for treating hair including, for example, compositions, kits, and methods for conditioning hair to impart conditioning and styling including beneficial properties such as frizz control and hair manageability that include softness, smoothing, good combing properties, and retention of shape.

BACKGROUND

Many different types of hair styling products are commercially available that are aimed to help consumers achieve a desired look, including one or more of fuller hair, thicker hair, sleek and straight hair, frizz-free hair, and defined curls. These products are typically provided in forms that are applied after the shampooing and conditioning processes are completed. Consumers selected from traditional styling products that provide styling benefits such as shaping memory, hold, increased volume, and the like in order to achieve a desired look.

In one example, styling products are available that provide protection against external factors such as protection from moisture to minimize or reduce frizziness. To achieve this benefit, a water-resistant film or coating may be applied to the hair using film-forming polymers. Depending on the chemical make-up of the film-forming polymers, product formulations that include these polymers can tend to be viscous, i.e. as the concentration of the polymer increases its viscosity builds up rapidly. Translated to styling applications, as the solvent evaporates, the polymer solution becomes thicker on the hair surface, leaving a sticky or tacky film residue on the hair. This often leaves hair with a stiff and/or "crunchy" feeling (i.e. the films become hard and brittle and therefore have a crunchy feel or sound when manipulated), which is undesirable to many consumers.

Increasingly, consumers seek hair products that have a natural look and feel, impart good styling benefits to hair, are durable, and lack the drawbacks of current products, such as the stiff and crunchy effects created by the thick coatings of many styling products. Further, consumers seek products that offer multiple benefits, for example, combining frizz reduction and style hold with softening, straightening and curl definition. Thus, there is a need for styling products that can confer the benefits sought by consumers using more natural ingredients and in products that complement the shampooing, conditioning and styling requirements of their customers.

BRIEF SUMMARY

The instant disclosure relates to a hair care composition that includes a unique combination of components that function to impart desirable cosmetic properties to the hair and are delivered during the shampooing and conditioning process, in various ways such as a conditioner composition (replacing the traditional conditioner products), or as a treatment in between shampooing and conditioning the hair, or after conditioning the hair.

In accordance with the various embodiments, the hair care composition is useful for providing a faster routine with fewer steps to achieve style, and the benefits of long-lasting style with a natural look and feel. In other various embodiments, the hair care composition is useful for enhancing and complimenting the shampooing/conditioning process. In particular, the benefits realized include but are not limited to frizz control, shape, discipline, style memory, and hair alignment to achieve looks that include hair smoothing, straightening, softening, and curl definition styling benefits. Also, consumers find the natural look and feel of hair treated with the compositions to be very appealing. In the various embodiments, that may include one or more additional components selected from fatty compounds, cationic polymers and styling polymers, the composition may be embodied to deliver one or more of smoothing, straightening and curling/curl defining style features.

The composition according to the disclosure comprises, in various embodiments, a novel association of polysaccharide, for example, inulin, and a film-forming polymer, in some embodiments at least one film-forming aminosilicone polymer formed by the reaction between a glycidoxypropyl-terminated dimethyl siloxane polymer, PEG-13 diglycidyl ether, diethylaminopropylamine, and aminopropyltriisopropoxysilane, for example polysilicone-29. The composition also includes one or more at least one anionic compound, at least one amphoteric compound, and at least one polymer compound other than above-described polysaccharide and film-forming polymer. This novel association exhibits synergy to create a hydrophobic film on the hair that confers softening and styling control to achieve styles that include one or more of hair smoothing, straightening, defined curl, and damage protection with a long-lasting effect. In the various embodiments, that may include one or more additional components selected from fatty compounds, styling polymers, the composition may be embodied to deliver one or more of smoothing, straightening and curling/curl defining style features to achieve a particular straight or curly style with frizz control, softness and manageability.

In accordance with some embodiments, the hair care composition includes:
a. at least one polysaccharide;
b. at least one film-forming aminosilicone polymer formed by the reaction between a glycidoxypropyl-terminated dimethyl siloxane polymer, PEG-13 diglycidyl ether, diethylaminopropylamine, and aminopropyltriisopropoxysilane; and
c. water.

In accordance with some such embodiments, the at least one polysaccharide is a plant gum selected from inulin, carrageenan, and pullulan and combinations thereof, and the at least one film-forming aminosilicone polymer is polysilicone-29.

In accordance with some such embodiments, the at least one polysaccharide is present in an amount from about 0.2% to about 10% by weight of the composition; and the at least one film-forming aminosilicone polymer is present in an amount from about 0.5% to about 20% by weight of the composition.

In accordance with some such embodiments, the composition comprises at least one silicone other than the film-forming aminosilicone polymer formed by the reaction between a glycidoxypropyl-terminated dimethyl siloxane polymer, PEG-13 diglycidyl ether, diethylaminopropylamine, and aminopropyltriisopropoxysilane. In some embodiments, the at least one silicone is present from about 0.1% to about 8% by weight of the composition.

In accordance with some such embodiments, the composition comprises a cosmetically acceptable carrier comprising water and one or more water soluble solvents. In some particular embodiments, the water-soluble solvents may include glycols, in some specific embodiments comprising glycerin, ethylhexylglycerin, caprylyl glycol, dipropylene glycol, propylene glycol, butylene glycol, and combinations thereof.

In some particular embodiments, the composition is a non-ionic system. In some particular embodiments, the composition that is a nonionic system includes one or more polymers that include hydroxypropyl guar, hydroxyethylcellulose, modified potato starch, and at least one silicone, for example a combination of silicones comprising phenyl trimethicone, dimethicone, and dimethicone (and) dimethiconol.

In accordance with some embodiments, hair care composition includes:
a. at least one polysaccharide;
b. at least one film-forming aminosilicone polymer formed by the reaction between a glycidoxypropyl-terminated dimethyl siloxane polymer, PEG-13 diglycidyl ether, diethylaminopropylamine, and aminopropyltriisopropoxysilane;
c. water, present in an amount ranging from at least 20% by weight to about 80% by weight based on the total weight of the composition; and
d. one or more of at least one polymer selected from nonionic polymers, anionic polymers, and combinations thereof, and at least one amphoteric surfactant.

In accordance with some such embodiments, the at least one polysaccharide is a plant gum selected from inulin, carrageenan, and pullulan and combinations thereof, and the at least one film-forming aminosilicone polymer is polysilicone-29.

In accordance with some such embodiments, the at least one polysaccharide is present in an amount from about 0.2% to about 10% by weight of the composition; the at least one surfactant comprising an amphoteric surfactant is present in an amount from about 0.5% to about 20% by weight of the composition; and the at least one film-forming aminosilicone polymer is present in an amount from about 0.5% to about 20% by weight of the composition.

In an embodiment, the composition comprises at least one polymer including one or more anionic polymers such as polyacrylamide, and further comprises one or more of at least one fatty compound, at least one silicone, at least one nonionic surfactant, at least one water-soluble solvent comprising polyols, at least one emulsifier such as octyldodecanol and octyldodecyl xyloside, and combinations thereof.

In an embodiment, the composition comprises at least one polymer including one or more nonionic polymers chosen from hydroxypropyl guar, hydroxyethylcellulose, modified potato starch, and combinations thereof and further comprises one or more of at least one fatty compound, at least one silicone, at least one nonionic surfactant, at least one water-soluble solvent comprising polyols, and combinations thereof.

In an embodiment, the composition comprises at least one amphoteric surfactant chosen from of betaines, alkyl sultaines, alkyl amphoacetates, alkyl amphoprionates, salts thereof, and combinations thereof and further comprises one or more of at least one fatty compound, at least one silicone, at least one nonionic surfactant, at least one water-soluble solvent comprising polyols, and combinations thereof.

In accordance with some such embodiments, the composition comprises at least one fatty compound. In some embodiments, the at least one fatty compound is present from about 0.1% to about 10% by weight of the composition.

In accordance with some such embodiments, the composition comprises at least one silicone. In some embodiments, the at least one silicone is present from about 0.1% to about 8% by weight of the composition.

In accordance with some such embodiments, the composition comprises a cosmetically acceptable carrier comprising water and one or more water soluble solvents. In some particular embodiments, the water-soluble solvents may include glycols, in some specific embodiments comprising glycerin, ethylhexylglycerin, caprylyl glycol, dipropylene glycol, propylene glycol, butylene glycol, and combinations thereof.

In some particular embodiments, the composition is a water in oil emulsion comprising an anionic system that includes at least one nonionic surfactant or a combination of non-ionic surfactants and emulsifier additive. According to some such embodiments, the non-ionic surfactants include PEG-30 dipolyhydroxystearate, and the composition further includes the emulsifier octyldodecanol (and) octyldodecyl xyloside. In some particular embodiments, the composition includes the anionic polymer polyacrylamide in combination with C13-14 isoparaffin (and) laureth-7, and hydrogenated polyisobutene, and one or more fatty compounds, for example, mineral oil.

In some particular embodiments, the composition is an amphoteric system that includes at least one or a combination of amphoteric surfactants. According to some such embodiments, the amphoteric surfactants include sodium cocoamphopropionate. In some particular embodiments, the composition includes one or more polymers that include the anionic polymer polyacrylamide in combination with C13-14 isoparaffin (and) laureth-7 and PEG-120 methyl glucose trioleate.

In some particular embodiments, the composition is an anionic system that includes in the at least one surfactant one or a combination of non-ionic surfactants. According to some such embodiments, the non-ionic surfactants include PEG-40 hydrogenated castor oil. In some particular embodiments, the composition includes anionic polymers that include polyacrylamide (and) C13-14 isoparaffin (and) laureth-7, and one or more silicones, for example a combination of silicones comprising phenyl trimethicone, dimethicone, and dimethicone (and) dimethiconol.

In accordance with the various embodiments, the composition may comprise additional components such as active compounds, fragrance, preservatives may be included. In some embodiments, the composition comprises potassium hydroxide; sodium hydroxide; acetamide mea; lactic acid; taurine; citric acid; gluconolactone; fragrance; one or more preservatives comprising chlorhexidine dihydrochloride, phenoxyethanol, benzoic acid; one or more silicone compounds comprising lauryl PEG/PPG-18/18 dimethicone, dimethicone (and) dimethiconol, amodimethicone (and) trideceth-6 (and) cetrimonium chloride, aminopropyl triethoxysilane, dimethicone (and) amodimethicone (and) trideceth-10 (and) peg-100 stearate (and) steareth-6 (and) trideceth-3; and combinations thereof.

The hair care composition, in various embodiments, is unique in the ability to provide hair with improved manageability, long-lasting style and frizz control, and protection. Accordingly, the instant disclosure relates to methods for treating hair, for example, for improving the manageability of hair, for imparting lasting style and frizz control. More specifically, the hair care compositions may be used in methods for conditioning the hair, providing curl definition to the hair, providing frizz control to the hair, improving ease of combability and detangling, protecting the hair from damage, including heat damage, and increasing the appearance of hair volume.

The methods of treating hair according to the disclosure include application of the compositions of the present disclosure to shampooed hair, together or mixed with a conventional conditioner followed by rinsing from the hair, or in place of the conventional conditioner (and optionally followed by a treatment with a conventional conditioner), or after application and rinsing of a conventional conditioner, all optionally followed by rinsing.

DESCRIPTION

The composition in accordance with the disclosure provides unexpected and lasting benefits for hair styling when used as a rinse off product incorporated into an anionic, nonionic or amphoteric based conditioner system that is in some embodiments and oil in water emulsion or suspension. The unexpected benefits realized include but are not limited to frizz control, shape, discipline, style memory, and hair alignment to achieve looks that include hair smoothing, straightening, softening, and curl definition.

Managing, controlling, styling hair is something consumers must deal with on a daily basis, which typically involves daily time commitments to shampoo, condition, and style, which may include one or more of blow-dry and flat iron use in order to achieve a desired look. With the help of traditional hair styling products such as gels, mousse, sprays, creams, waxes, paste, balms and serums the desired style can be achieved, but they constitute additional steps in grooming the hair after the shampooing/conditioning process.

To address this context, a built-in treatment product that can provide styling, shaping, and manageability benefits to hair during the shampooing/conditioning process has been developed, as described herein. The composition according to the instant disclosure, embodied in a conditioner system or used in between a shampoo and a conditioner, enables a lifestyle enhancement for consumers by providing a novel rinse-off styling technology for hair care and styling. The composition, in various embodiments, includes components which create a hydrophobic film on the hair that imparts one or more of benefits. The composition can be used in the shower/shampooing care process as a combined conditioning and hair styling treatment which imparts softness, smoothing, good combing properties, and after drying hair, keeps hair soft, styled, shaped and smooth feeling with a long-lasting benefit that is retained through at least one shampooing, wherein shaping includes one or more of straightening and curling. Accordingly, the composition allows a consumer to have a simplified routine, integrating conditioning with styling and style manageability. The composition also provides protection to the hair from damage, for example, damage caused by heat, environmental stress, etc. And the benefits of the composition, in the various embodiments, are long lasting, as styled hair treated with the composition can survive washing or rinsing. Thus, hair maintains the desirable cosmetic properties imparted by the hair care compositions until the next shampooing, rinsing, etc.

Salon trials have shown that the composition, in various embodiments, delivers unexpected performance that includes long lasting style, ease of styling, frizz control, and enables the consumer to achieve hair styling with a natural look and feel without crunch. Also unexpectedly, the composition provides a "salon grade" look, that includes smoothing the hair and retained holding of style longer, i.e., even after rinsing the hair; the hair looks shiny, soft and smooth from root to tip, it also aligns the hair from root to tip. Further, as described in the exemplified embodiments, the styling compositions show a benefit for a wide range of curl patterns and demographics, providing for well defined, frizz free curls that unexpectedly exceed consumers' expectations in delivering superior long-lasting benefits. Hair is easy to detangle, soft, shiny, bouncy with movement, including well-defined curls and no frizz.

Hair Care Composition.

The composition according to the disclosure comprises, in various embodiments, water that is, in some embodiments, present at a level of at least 20% by weight of composition. The composition also includes in an anionic, nonionic or amphoteric system a novel association of polysaccharide, for example, Inulin, and a film-forming polymer, for example polysilicone-29. In some particular embodiments, the composition includes one or a combination of surfactants that include one or more anionic, nonionic or amphoteric surfactants. This novel association exhibits synergy to create a hydrophobic film on the hair that confers softening and styling control to achieve styles that include one or more of hair smoothing, straightening, defined curl, and damage protection with a long-lasting effect. In the various embodiments, that may include one or more additional components selected from fatty compounds, and styling polymers, the composition may be embodied to deliver one or more of smoothing, straightening and curling/curl defining style features.

While not wishing to be bound by any particular theory, it is posited that the compositions provide the hair with a hydrophobic, flexible, film or film-like coating that is long-lasting, has a very natural look and feel, and improves the styling properties of the hair. The compositional components that include the polysaccharide and the film-forming polymer contribute to the lightweight texture and provides the smooth hair. Addition of fatty compounds and one or more of anionic polymers and/or nonionic polymers and/or amphoteric and nonionic surfactants confer additional benefits to achieve styling and one or more of control, and hair smoothing, and curl definition.

The hair care composition can be used at home during an individual's regular shampooing and/or conditioning routine and therefore do not require special procedures that are only available at professional salons. Accordingly, the instant disclosure relates to individual products that comprise the composition in a conditioner vehicle, and kits that include a hair care composition of the instant disclosure together with other compositions. The kits typically include at least one hair care composition according to the instant disclosure (a hair care composition comprising one or more polysaccharides, one or more nonionic or amphoteric surfactants, one or more anionic or nonionic polymers, and water, etc.) and one or more additional hair care compositions, for example, a shampoo. The various hair care compositions are separately contained in the kits. In some instances, the kits include one or more hair care compositions (according the instant disclosure) and a shampoo, each of which are separately contained.

(a) Polysaccharide

In accordance with the disclosure, the hair care composition includes in the various embodiments at least one polysaccharide. In general, the polysaccharide may be chosen from polysaccharides isolated from algae, polysaccharides produced by microorganisms, and polysaccharides from higher plants, such as homogeneous polysaccharides. In particular, the polysaccharides may be chosen from fructans, galactans, pullulan, and derivatives thereof. In other examples, the polysaccharides may comprise methylcelluloses, hydroxyalkylcelluloses, ethylhydroxyethylcelluloses and carboxymethylcelluloses, mannans, xylans, lignins, arabans, galacturonans, alginate-based compounds, chitin, chitosans, glucuronoxylans, arabinoxylans, xyloglucans, glucomannans, pectic acids and pectins, arabinogalactans, agars, glycosaminoglycans, gum arabics, tragacanth gums, ghatti gums, karaya gums, locust bean gums, galactomannans such as guar gums and nonionic derivatives thereof, in particular hydroxypropyl guar, and ionic derivatives thereof, biopolysaccharide gums of microbial origin, in particular scleroglucan or xanthan gums, mucopolysaccharides, and in particular chondroitin sulfates, and mixtures thereof.

In some embodiments, the at least one polysaccharide may be chosen from fructans, galactans, pullulan, derivatives thereof and combinations thereof.

According to the various embodiments, the at least one polysaccharide may be chemically modified, especially with urea or urethane groups, or by a hydrolysis, oxidation, esterification, etherification, sulfatation, phosphatation, amination, amidation or alkylation reaction, or by several of these modifications. The derivatives obtained may be anionic, cationic, amphoteric or nonionic.

Polysaccharides Isolated from Algae: Fructosans

In some particular embodiments, the polysaccharide according to the invention may especially be a fructosan chosen from inulin and derivatives thereof (especially dicarboxy and carboxymethyl inulins). Fructans or fructosans are oligosaccharides or polysaccharides comprising a sequence of anhydrofructose units optionally combined with several saccharide residues other than fructose. Fructans may be linear or branched. Fructans may be products obtained directly from a vegetable or microbial source or alternatively products whose chain length has been modified (increased or decreased) by fractionation, synthesis or hydrolysis, in particular enzymatic. Fructans generally have a degree of polymerization from 2 to about 1000 and, in some embodiments, from 2 to about 60.

Three groups of fructans are distinguished. The first group corresponds to products whose fructose units are for the most part linked via β(2,1) bonds. These are essentially linear fructans such as inulins. The second group also corresponds to linear fructoses, but the fructose units are essentially linked via β(2,6) bonds. These products are levans. The third group corresponds to mixed fructans, i.e. fructans containing β(2,6) and β(2,1) sequences. These are essentially branched fructans, such as graminans. Inulin is also referred to technically as Alantin, Fructosane, Synantherin, and Synanthrin Inulin may be obtained, for example, from chicory, dahlia or Jerusalem artichoke, in some embodiments, from chicory. Inulin is the polysaccharide that conforms to the formula:

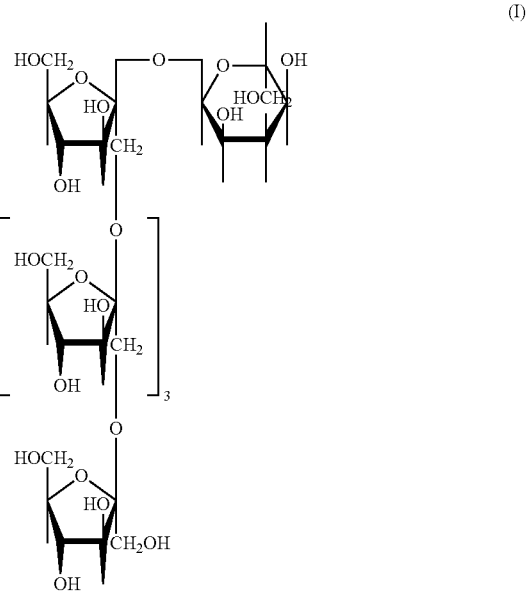

(I)

In particular, the polysaccharide, especially the inulin, has a degree of polymerization from 2 to about 1000 and, in some embodiments, from 2 to about 60, and a degree of substitution of less than 2 on the basis of one fructose unit. The inulin used for this invention is represented, for example, by the products available under the tradename INUTEC H25P (CREACHEM), also sold under the name Beneo™ Inulin by the company Orafti, and under the name Frutafit® by the company Sensus.

TABLE 1

| Inulin Properties vs Polyurethane and PVP | | | |
|---|---|---|---|
| Property | Inulin | PU34 | PVP |
| Hardness (flexibility; three-point bending test) | 40.75 | 70 | 203.25 |
| Hydrophobicity (Contact Angle) | 117.84 | 91.45 | 57.11 |

Polysaccharides Isolated from Algae: Galactans

In some particular embodiments, the polysaccharide according to the invention may be a galactan chosen especially from agar and carrageenans. Galactans of agar type are galactose polysaccharides contained in the cell wall of some of these species of red algae (Rhodophyceae) belonging to the Gigartinaceae, Hypneaceae, Furcellariaceae and Polyideaceae families. They are formed from a polymer group in which the base backbone is a β(1,3) D-galactopyranose and α(1,4) L 3-6 anhydrogalactose chain, these units repeating regularly and alternately. The differences within the agar family are due to the presence or absence of methyl or carboxyethyl solvated groups. These hybrid structures are generally present in variable percentage, depending on the species of algae and the season of harvest.

They are generally obtained by hot aqueous extraction from natural strains of the said algae. These linear polymers, formed by disaccharide units, are composed of two D-galactopyranose units alternately linked via α(1,3) and β(1,4)

bonds. These are highly sulfated polysaccharides (20-50%) and the α-D-galactopyranosyl residues may be in 3,6-anhydro form. According to the number and position of the ester sulfate groups on the repeat disaccharide of the molecule, several types of carrageenan are distinguished, namely: kappa-carrageenans, which bear one ester sulfate group, iota-carrageenans which bear two ester sulfate groups, and lambda-carrageenans which bear three ester sulfate groups.

Carrageenans are composed essentially of potassium, sodium, magnesium, triethanolamine and/or calcium salts and of ester sulfates of polysaccharides. Carrageenans are sold especially by the company SEPPIC under the name Solagum®, by the company Gelymar under the names Carragel®, Carralact® and Carrasol®, by the company Cargill under the names Satiagel™ and Satiagum™, and by the company CP-Kelco under the names Genulacta®, Genugel® and Genuvisco®.

Polysaccharides Produced by Microorganisms: Pullulan

In some particular embodiments, the polysaccharide according to the invention may be pullulan. Pullulan is a polysaccharide consisting of maltotriose units, known under the name α(1,4)-α(1,6)-glucan. Three glucose units in maltotriose are connected via an α(1,4) glycosidic bond, whereas the consecutive maltotriose units are connected to each other via an α(1,6) glycosidic bond. Pullulan is produced, for example, under the reference Pullulan PF 20 by the company Hayashibara in Japan.

In general, the compounds of this type that may be used in the present invention are chosen from those described especially in Kirk-Othmer's *Encyclopedia of Chemical Technology*, Third Edition, 1982, volume 3, pp. 896-900, and volume 15, pp. 439-458, in *Polymers in Nature* by E. A. McGregor and C. T. Greenwood, published by John Wiley & Sons, Chapter 6, pp. 240-328, 1980, in the publication by Robert L. Davidson entitled *Handbook of Water-soluble Gums and Resins* published by McGraw-Hill Book Company (1980) and in *Industrial Gums—Polysaccharides and their Derivatives*, edited by Roy L. Whistler, Second Edition, published by Academic Press Inc.

In accordance with the various embodiments, the amount of each of the at least one polysaccharide present in the compositions can range from about 0.5% to about 10%, or from about 0.5% to about 7%, or from about 1% to about 3.5% or any suitable combination, sub-combination, range, or sub-range thereof by weight, based on the weight of the composition. One of ordinary skill in the art, however, will appreciate that other ranges are within the scope of the invention.

In accordance with the various embodiments, the total amount of polysaccharide present in the compositions can range from about 0.5% to about 20%, or from about 0.5% to about 10%, or from about 0.5% to about 5%, or from about 1% to about 3% or any suitable combination, sub-combination, range, or sub-range thereof by weight, based on the weight of the composition. One of ordinary skill in the art, however, will appreciate that other ranges are within the scope of the invention.

Thus, any one of the at least one polysaccharide is present, by weight, based on the total weight of the composition, from about 0.5, 0.6, 0.7, 0.8, 0.9, 1, 2, 3, 4, 5, 6, 7, 8, 9, to about 10 weight percent, including increments and ranges therein and there between.

(b) Film-Forming Aminosilicone Polymer

In accordance with the disclosure, the hair care composition includes in the various embodiments at least one film-forming aminosilicone polymer.

In accordance with some embodiments, the at least one film-forming aminosilicone polymer comprises Polysilicone-29, which is a film-forming aminosilicone polymer formed by the reaction between a glycidoxypropyl-terminated dimethyl siloxane polymer, PEG-13 diglycidyl ether, diethylaminopropylamine, and aminopropyltriisopropoxysilane sold under the tradename SILSOFT CLX-E emulsion (Momentive Performance Materials).

In accordance with the various embodiments, the amount of each of the at least one film-forming aminiosilicone polymer is from about 0.5% to about 20%, or from about 0.5% to about 15%, or from about 1% to about 10%, or from about 2% to about 5% or any suitable combination, sub-combination, range, or sub-range thereof by weight, based on the weight of the composition. One of ordinary skill in the art, however, will appreciate that other ranges are within the scope of the invention.

In accordance with the various embodiments, the total amount of film-forming aminiosilicone polymer present in the compositions can range from about 0.5% to about 40%, or from about 0.5% to about 20%, or from about 0.5% to about 10%, or from about 1% to about 5% or any suitable combination, sub-combination, range, or sub-range thereof by weight, based on the weight of the composition. One of ordinary skill in the art, however, will appreciate that other ranges are within the scope of the invention.

Thus, any one of the at least one film-forming aminiosilicone polymer is present, by weight, based on the total weight of the composition, from about 0.5, 0.6, 0.7, 0.8, 0.9, 1, 2, 3, 4, 5, 6, 7, 8, 9, 10, 11, 12, 13, 14, 15, 16, 17, 18, 19, to about 20 weight percent, including increments and ranges therein and there between.

(c) Amphoteric and Nonionic Surfactants

In accordance with the disclosure, the hair care composition may include at least one surfactant selected from anionic, non-ionic and amphoteric surfactants.

In some embodiments, the at least one surfactant includes one or more non-ionic surfactants comprising PEG-30 dipolyhydroxystearate.

In some embodiments, the at least one surfactant includes one or more non-ionic surfactants comprising PEG-40 hydrogenated castor oil.

In some embodiments, the at least one surfactant includes one or more amphoteric surfactants comprising. sodium cocoamphopropionate.

A more exhaustive list of surfactants that may be included in the hair care compositions is provided hereinbelow, under the headings "Non-ionic Surfactants" and "Amphoteric Surfactants."

In accordance with some embodiments, the amount of each of the at least one surfactant is from about 0.1% to about 15%, or from about 0.2% to about 10%, or from about 0.2% to about 5%, or from about 0.5% to about 3% or any suitable combination, sub-combination, range, or sub-range thereof by weight, based on the weight of the composition. One of ordinary skill in the art, however, will appreciate that other ranges are within the scope of the invention.

In accordance with the various embodiments, when present, the total amount of surfactant present in the compositions can range from about 0.1% to about 25%, or from about 0.1% to about 10%, or from about 0.1% to about 5%, or from about 0.5% to about 3% or any suitable combination, sub-combination, range, or sub-range thereof by weight, based on the weight of the composition. One of ordinary skill in the art, however, will appreciate that other ranges are within the scope of the invention.

Thus, any one of the at least one surfactant is present, by weight, based on the total weight of the composition, from about 0.1, 0.2, 0.3, 0.4, 0.5, 0.6, 0.7, 0.8, 0.9, 1, 2, 3, 4, 5, 6, 7, 8, 9, 10, 11, 12, 13, 14, to about 15 weight percent, including increments and ranges therein and there between.

Amphoteric Surfactants

In certain embodiments when the hair treatment composition of the present disclosure is a shampoo or a cleansing composition that contains at least one amphoteric surfactant. The amphoteric surfactants may, for example, be selected from betaines, alkyl sultaines, alkyl amphoacetates and alkyl amphodiacetates, alkyl amphoprionates, salts thereof, or mixtures thereof.

In various embodiments, the betaines are selected from alkyl betaines, alkyl amidopropyl betaines, alkyl sulfobetaines (sultaines), or mixtures thereof.

In an embodiment, the amphoteric surfactants are selected from cocamidopropyl betaine, coco-betaine, or mixtures thereof.

If present, the total amount of amphoteric surfactant(s) in the compositions may vary, but is typically from about 0.05 to about 10 wt %, based on the total weight of the composition. In some instance, the total amount of amphoteric surfactant(s) in the composition is from about 0.05 to about 8 wt %, from about 0.1 to about 7 wt %, from about 0.1 to about 6 wt %, from about 0.15 to about 6 wt %, from about 0.15 to about 5 wt %, from about 0.15 to about 4 wt %, from about 0.15 to about 3 wt %, or from about 0.2 to about 2.5 wt %, based on the total weight of the composition, including ranges and sub-ranges therebetween.

Betaines

Exemplary useful betaines include, but are not limited to, those of the following formula:

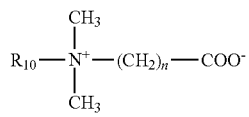
(II)

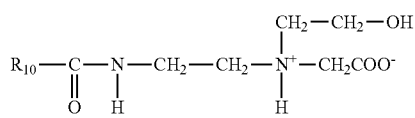
(III)

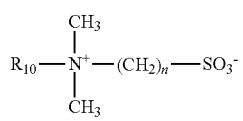
(IV)

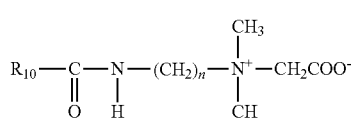
(V)

wherein:
$R_{10}$ is an alkyl group having from 8-18 carbon atoms; and
n is an integer from 1 to 3.

Particularly useful betaines include, for example, cocobetaine, cocamidopropyl betaine, lauryl betaine, laurylhydroxy sulfobetaine, lauryldimethyl betaine, cocamidopropyl hydroxysultaine, behenyl betaine, capryl/capramidopropyl betaine, lauryl hydroxysultaine, stearyl betaine, or mixtures thereof. Particularly preferred betaines include coco-betaine and cocamidopropyl betaine.

Alkyl Sultaines

Non-limiting examples of alkyl sultaines include hydroxyl sultaines of formula:

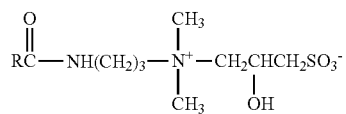
(VI)

wherein R is an alkyl group having 8-18 carbon atoms.

More specific examples include, but are not limited to cocamidopropyl hydroxysultaine, lauryl hydroxysultaine, or mixtures thereof.

Alkyl Amphoacetates and Alkyl Amphodiacetates

Useful alkyl amphoacetates and alkyl amphodiacetates include those of formulae:

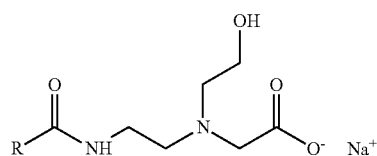
(VII)

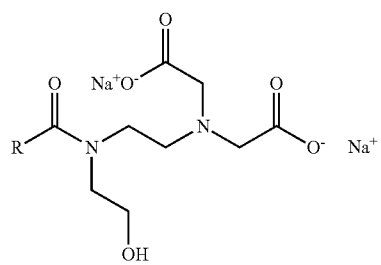
(VIII)

wherein R is an alkyl group having 8-18 carbon atoms. Although sodium is shown as the cation in the above formulae, the cation may be any alkali metal ion, such as sodium or potassium, ammonium ions, or alkanolammonium ions such as monoethanolammonium or triethanolammonium ions. A non-limiting example is sodium lauroamphoacetate.

Alkyl Amphopropionates

Exemplary and non-limiting examples of useful alkyl amphopropionates include cocoamphopropionate, caprylamphopropionate, cornamphopropionate, caproampho-propionate, oleoamphopropionate, isostearoamphopropionate, stearoamphopropionate, lauroamphopropionate, salts thereof, or mixtures thereof.

Nonionic Surfactants

The hair treatment compositions of the present disclosure may include at least one nonionic surfactant.

The nonionic surfactant(s) can be, for example, selected from alkyl polyglucosides, fatty amide, fatty alcohols, alpha-diols, alkylphenols and esters of fatty acids, being ethoxylated, propoxylated or glycerolated and having at least one fatty chain comprising, for example, from 8 to 18 carbon atoms, it being possible for the number of ethylene oxide or propylene oxide groups to range from 2 to 50, and for the number of glycerol groups to range from 1 to 30. Maltose derivatives may also be mentioned. Non-limiting mention may also be made of copolymers of ethylene oxide and/or of propylene oxide; condensates of ethylene oxide and/or of propylene oxide with fatty alcohols; polyethoxylated fatty amides comprising, for example, from 2 to 30 mol of ethylene oxide; polyglycerolated fatty amides comprising, for example, from 1.5 to 5 glycerol groups, such as from 1.5 to 4; ethoxylated fatty acid esters of sorbitan comprising from 2 to 30 mol of ethylene oxide; ethoxylated oils from plant origin; fatty acid esters of sucrose; fatty acid esters of polyethylene glycol; polyethoxylated fatty acid mono or diesters of glycerol ($C_6$-$C_{24}$)alkylpolyglycosides; N—($C_6$-$C_{24}$)alkylglucamine derivatives, amine oxides such as ($C_{10}$-$C_{14}$)alkylamine oxides or N—($C_{10}$-$C_{14}$)acylaminopropylmorpholine oxides, or mixtures thereof.

Such nonionic surfactants may in some embodiments be chosen from polyoxyalkylenated or polyglycerolated nonionic surfactants. The oxyalkylene units are more particularly oxyethylene or oxypropylene units, or a combination thereof, and are in some embodiments oxyethylene units.

In some cases, the nonionic surfactant may be selected from esters of polyols with fatty acids with a saturated or unsaturated chain containing for example from 8 to 24 carbon atoms, in some embodiments 12 to 22 carbon atoms, and alkoxylated derivatives thereof, in some embodiments with a number of alkyleneoxide of from 10 to 200, and in some embodiments from 10 to 100, such as glyceryl esters of a $C_8$-$C_{24}$, in some embodiments $C_{12}$-$C_{22}$, fatty acid or acids and alkoxylated derivatives thereof, in some embodiments with a number of alkyleneoxide of from 10 to 200, and in some embodiments from 10 to 100; polyethylene glycol esters of a $C_8$-$C_{24}$, in some embodiments $C_{12}$-$C_{22}$, fatty acid or acids and alkoxylated derivatives thereof, in some embodiments with a number of alkyleneoxide of from 10 to 200, and in some embodiments from 10 to 100; sorbitol esters of a $C_8$-$C_{24}$, in some embodiments $C_{12}$-$C_{22}$, fatty acid or acids and alkoxylated derivatives thereof, in some embodiments with a number of alkyleneoxide of from 10 to 200, and in some embodiments from 10 to 100; sugar (sucrose, glucose, alkylglycose) esters of a $C_8$-$C_{24}$, in some embodiments $C_{12}$-$C_{22}$, fatty acid or acids and alkoxylated derivatives thereof, in some embodiments with a number of alkyleneoxide of from 10 to 200, and in some embodiments from 10 to 100; ethers of fatty alcohols; ethers of sugar and a $C_8$-$C_{24}$, in some embodiments $C_{12}$-$C_{22}$, fatty alcohol or alcohols; or mixtures thereof.

Examples of ethoxylated fatty esters that may be mentioned include the adducts of ethylene oxide with esters of lauric acid, palmitic acid, stearic acid or behenic acid, or mixtures thereof, especially those containing from 9 to 100 oxyethylene groups, such as PEG-9 to PEG-50 laurate (as the CTFA names: PEG-9 laurate to PEG-50 laurate); PEG-9 to PEG-50 palmitate (as the CTFA names: PEG-9 palmitate to PEG-50 palmitate); PEG-9 to PEG-50 stearate (as the CTFA names: PEG-9 stearate to PEG-50 stearate); PEG-9 to PEG-50 palmitostearate; PEG-9 to PEG-50 behenate (as the CTFA names: PEG-9 behenate to PEG-50 behenate); polyethylene glycol 100 EO monostearate (CTFA name: PEG-100 stearate); or mixtures thereof.

As glyceryl esters of fatty acids, glyceryl stearate (glyceryl mono-, di- and/or tristearate) (CTFA name: glyceryl stearate) or glyceryl ricinoleate or mixtures thereof can in particular be cited.

As glyceryl esters of $C_8$-$C_{24}$ alkoxylated fatty acids, polyethoxylated glyceryl stearate (glyceryl mono-, di- and/or tristearate) such as PEG-20 glyceryl stearate can for example be cited.

Mixtures of these surfactants, such as for example the product containing glyceryl stearate and PEG-100 stearate, marketed under the name ARLACEL 165 by Uniqema, and the product containing glyceryl stearate (glyceryl mono- and distearate) and potassium stearate marketed under the name TEG1 N by Goldschmidt (CTFA name: glyceryl stearate SE), can also be used.

Useful alkyl polyglucosides include those having the following formula:

$$R^1\text{—}O\text{—}(R^2O)_n\text{—}Z(x) \qquad (IX)$$

wherein:

$R^1$ is an alkyl group having 8-18 carbon atoms;

$R^2$ is an ethylene or propylene group;

Z is a saccharide group with 5-6 carbon atoms;

n is an integer ranging from 0 to 10; and x is an integer ranging from 1 to 5.

Useful alkylpolyglucosides include lauryl glucoside, octyl glucoside, decyl glucoside, coco glucoside, caprylyl/capryl glucoside, sodium lauryl glucose carboxylate, or mixtures thereof. Typically, the alkyl polyglucoside compound is selected from the group consisting of lauryl glucoside, decyl glucoside, coco glucoside, or mixtures thereof. In some instances, decyl glucoside is particularly preferred.

The fatty alcohols that may be used in the composition of the disclosure include, but are not limited to, non-alkoxylated, saturated or unsaturated, linear or branched, and have from 6 to 60 carbon atoms, such as from 8 to 30 carbon atoms.

The fatty alcohols of the present disclosure are chosen from solid and liquid fatty alcohols.

The saturated liquid fatty alcohols can be branched. They can optionally comprise, in their structure, at least one aromatic or non-aromatic ring. They can be acyclic.

The unsaturated liquid fatty alcohols exhibit, in their structure, at least one double or triple bond, and in some embodiments one or more double bonds. When several double bonds are present, there are in some embodiments 2 or 3 of them and they can be conjugated or unconjugated. These unsaturated fatty alcohols can be linear or branched. They can optionally comprise, in their structure, at least one aromatic or non-aromatic ring. They can be acyclic. Among the liquid unsaturated fatty alcohols, oleyl alcohol, linoleyl alcohol, linolenyl alcohol and undecylenyl alcohol may be mentioned.

Liquid fatty alcohols may be selected, for example, from octyldodecanol, 2-butyloctanol, 2-hexyldecanol, 2-undecylpentadecanol, oleyl alcohol or linoleyl alcohol, isostearyl alcohol, or mixtures thereof.

Solid fatty alcohols may be crystalline, amorphous, or pasty. The solid fatty alcohols of the present invention are solid at room temperature (25° C.) and at atmospheric pressure (1 atm), and are insoluble in water (i.e. they have a solubility in water of less than 1% by weight and in some embodiments less than 0.5% by weight, at 25° C. and 1 atm) and are soluble, under the same temperature and pressure conditions, in at least one organic solvent (for example ethanol, chloroform, benzene, or liquid petroleum jelly) to at least 1% by weight.

In one embodiment, the solid fatty alcohols in some embodiments have a melting point of greater than or equal to 28° C. and have a viscosity, at a temperature of 40° C. and at a shear rate of 1 $s^{-1}$, of greater than or equal to 1 Pa·s.

In an embodiment, the melting point of the fatty alcohols ranges from 30° C. to 250° C., such as from 32° C. to 150° C., or from 35° C. to 150° C.

The melting points may be measured by DSC or on a Kofler bench. The melting point may be measured by differential calorimetric analysis (DSC) with a temperature rise of 10° C. per minute. The melting point is then the temperature corresponding to the top of the melting endotherm peak obtained during the measurement.

The viscosity measurements may be taken at a temperature of about 40° C. using an RS600 rheometer from Thermoelectron.

The solid fatty alcohols of the present invention are chosen from saturated or unsaturated, linear or branched, in some embodiments linear and saturated, (mono) alcohols comprising from 6 to 60 carbon atoms, such as from 10 to 50 carbon atoms, or from 12 to 24 carbon atoms.

The solid fatty alcohols in some embodiments have the structure of the following formula:

R—OH                                            (X)

in which R especially denotes a C6-C60, for example, C8-C60, and in some embodiments C10-O50 or even C12-C30 alkyl group, R possibly being substituted with one or more hydroxyl groups, R possibly being branched. The solid fatty alcohols of the invention may be non-oxyalkylenated and/or non-glycerolated. These fatty alcohols may be constituents of animal or plant waxes.

In some embodiments the solid fatty alcohol may represent a mixture of fatty alcohols, which means that several species of fatty alcohol may coexist, in the form of a mixture, in a commercial product. One example of such a commercial product is cetearyl alcohol, a mixture of cetyl alcohol and stearyl alcohol, commercially available under the trade name of LANETTE O OR from the company BASF. Cetyl alcohol may also be commercially available under the tradename of LANETTE 16 from the company BASF.

In an embodiment, the solid fatty alcohols of the present invention may be chosen from myristyl alcohol, cetyl alcohol, stearyl alcohol, cetearyl alcohol, or mixtures thereof, octyldodecanol, 2-butyloctanol, 2-hexyldecanol, 2-undecylpentadecanol, oleic alcohol, linoleic alcohol, behenyl alcohol, or mixtures thereof.

Other suitable examples of the solid fatty alcohol of the present invention include branched solid fatty alcohols chosen from 2-dodecylhexadecanol, 2-tetradecyl-1-octadecanol, 2-tetradecyl-1-eicosanol, 2-hexadecyl-1-octadecanol, and 2-hexadecyl-1-eicosanol, or mixtures thereof.

In some embodiments, the fatty alcohol is chosen from non-alkoxylated, saturated or unsaturated, linear or branched fatty alcohol having from 6 to 60 carbon atoms is chosen from cetyl alcohol, stearyl alcohol, cetearyl alcohol (mixture of cetyl alcohol and stearyl alcohol), octyldodecanol, 2-butyloctanol, 2-hexyldecanol, 2-undecylpentadecanol, oleic alcohol, linoleic alcohol, behenyl alcohol, 2-dodecylhexadecanol, 2-tetradecyl-1-octadecanol, 2-tetradecyl-1-eicosanol, 2-hexadecyl-1-octadecanol and 2-hexadecyl-1-eicosanol, octyldodecanol, 2-butyloctanol, 2-hexyldecanol, 2-undecylpentadecanol, oleyl alcohol or linoleyl alcohol, isostearyl alcohol, or mixtures thereof.

In some embodiments, the at least one nonionic surfactant is selected from alkyl polyglucosides, fatty alcohols, alkoxylated fatty alcohols, sorbitan derivatives, glyceryl esters, or mixtures thereof.

(d) Water/Cosmetically Acceptable Carrier

In accordance with the disclosure, the hair care composition includes in the various embodiments, water, and in some embodiments, one or more water-soluble solvents, or mixtures thereof in a cosmetically acceptable carrier.

Water

In accordance with the various embodiments water is present in total amounts of from about 60%, or from about 65%, or from about 70%, or from about 75%, or from about 80%, or from about 85%, or from about 90%, and up to about 99%, or up to about 95%, or up to about 90%, or up to about 85%, or up to about 80%, or up to about 75%, or up to about 70%. For example, water is present in amounts ranging from about 60% to about 99% by weight, about 70% to about 95% by weight, or about 60%, 70%, 75%, 80%, 85%, 90%, 95%, or 99% by weight, or any suitable combination, sub-combination, range, or sub-range thereof by weight, based on the weight of the composition. One of ordinary skill in the art, however, will appreciate that other ranges are within the scope of the invention.

Thus, any water is present, by weight, based on the total weight of the composition, from about 60, 61, 62, 63, 64, 65, 66, 67, 68, 69, 70, 71, 72, 73, 74, 75, 76, 77, 78, 79, 80, 85, 90, 95, to about 99 weight percent, including increments and ranges therein and there between.

Water-Soluble Solvents

In accordance with some embodiments, the hair treatment composition may include in the cosmetically acceptable carrier at least one water-soluble solvent. The term "water-soluble solvent" is interchangeable with the term "water-miscible solvent" and means a compound that is liquid at 25° C. and at atmospheric pressure (760 mmHg), and it has a solubility of at least 50% in water under these conditions. In some cases, the water-soluble solvent has a solubility of at least 60%, 70%, 80%, or 90% in water under these conditions. Non-limiting examples of water-soluble solvents include, for example, glycerin, alcohols (for example, C1-C30, C1-C15, C1-C10, or C1-C4 alcohols), organic solvents, polyols, glycols, or mixtures thereof.

As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

Further non-limiting examples of water-soluble solvents include alkanols (polyhydric alcohols such as glycols and polyols) such as glycerin, 1,2,6-hexanetriol, trimethylolpropane, ethylene glycol, propylene glycol, diethylene glycol, butylene glycol, hexylene glycol, triethylene glycol, tetraethylene glycol, pentaethylene glycol, dipropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, or mixtures thereof.

In some cases, the water-soluble solvent may be selected from the group consisting of one or more glycols, $C_{1-4}$ alcohols, glycerin, or mixtures thereof, for example, glycerin, ethylhexylglycerin, and mixtures thereof.

In accordance with the various embodiments total amount of the at least one water-soluble solvent, when present, may vary, but is typically from about 0.5% to about 25%, or from about 0.5% to about 20%, or from about 1% to about 20%, or from about 1% to about 10%, or from about 2% to about 5% or any suitable combination, sub-combination, range, or sub-range thereof by weight, based on the weight of the composition. In one embodiment, wherein the composition comprises at least one polymer present from about 0.1% to about 20% by weight of the composition and the at least one polymer comprises an anionic polymer, the composition comprises one or more water-soluble solvents comprising polyols present in an amount of at least 40% by weight. One of ordinary skill in the art, however, will appreciate that other ranges are within the scope of the invention.

Thus, any one water-soluble solvent, when present, is present, by weight, based on the total weight of the composition, from about 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24 to about 25 weight percent, including increments and ranges therein and there between.

Fatty Compounds

In accordance with the disclosure, the hair care composition may include in some embodiments one or more fatty compounds. In some particular embodiments, the fatty compounds include mineral oil.

In accordance with the various embodiments, when present, the amount of each of the at least one fatty compound is from about 0.1% to about 10%, or from about 0.1% to about 8%, or from about 0.2% to about 7%, or from about 1% to about 5%, or from about 1.5% to about 3% or any suitable combination, sub-combination, range, or sub-range thereof by weight, based on the weight of the composition. One of ordinary skill in the art, however, will appreciate that other ranges are within the scope of the invention.

In accordance with the various embodiments, the total amount of fatty compound present in the compositions can range from about 0.1% to about 15%, or from about 0.5% to about 12%, or from about 1% to about 10%, or from about 1.5% to about 5% or any suitable combination, sub-combination, range, or sub-range thereof by weight, based on the weight of the composition. One of ordinary skill in the art, however, will appreciate that other ranges are within the scope of the invention.

Thus, any one of the at least one fatty compound is present, by weight, based on the total weight of the composition, from about 8 0.2, 0.3, 0.4, 0.5, 0.6, 0.7, 0.8, 0.9, 1, 2, 3, 4, 5, 6, 7, 8, 9, to about 10 weight percent, including increments and ranges therein and there between.

Mineral oils, such as liquid paraffin or liquid petroleum, or animal oils, such as perhydrosqualene or arara oil, or alternatively of vegetable oils, such as sweet almond, calophyllum, palm, castor, avocado, jojoba, olive or cereal germ oil, may be utilized. It is also possible to use esters of these oils, e.g., jojoba esters. Also useful are esters of lanolic acid, of oleic acid, of lauric acid, of stearic acid or of myristic acid; esters of alcohols, such as oleyl alcohol, linoleyl or linolenyl alcohol, isostearyl alcohol or octyldodecanol; and/or acetylglycerides, octanoates, decanoates or ricinoleates of alcohols or of polyalcohols. It is alternatively possible to use hydrogenated oils which are solid at 25° C., such as hydrogenated castor, palm or coconut oils, or hydrogenated tallow; mono-, di-, tri- or sucroglycerides; lanolins; or fatty esters which are solid at 25° C.

More generally, fatty compounds that may be present include, in some embodiments, "non-silicone fatty compounds," i.e., fatty compounds that do not containing any silicon (Si) atoms. Non-limiting examples of non-silicone fatty compounds include oils, mineral oil, fatty acids, fatty alcohol derivatives, fatty acid derivatives (such as alkoxylated fatty acids or polyethylene glycol esters of fatty acids or propylene glycol esters of fatty acids or butylene glycol esters of fatty acids or esters of neopentyl glycol and fatty acids or polyglycerol/glycerol esters of fatty acids or glycol diesters or diesters of ethylene glycol and fatty acids or esters of fatty acids and fatty alcohols, esters of short chain alcohols and fatty acids), esters of fatty alcohols, hydroxy-substituted fatty acids, waxes, triglyceride compounds, lanolin, or mixtures thereof. Non-limiting examples of the fatty acids, fatty alcohol derivatives, and fatty acid derivatives are found in International Cosmetic Ingredient Dictionary, Sixteenth Edition, 2016, which is incorporated by reference herein in its entirety.

In some embodiments, fatty acids useful herein include those having from about 10 to about 30 carbon atoms, from about 12 to about 22 carbon atoms, and from about 16 to about 22 carbon atoms. These fatty acids can be straight or branched chain acids and can be saturated or unsaturated. Also included are diacids, triacids, and other multiple acids which meet the carbon number requirement herein. Also included herein are salts of these fatty acids. Nonlimiting examples of fatty acids include lauric acid, palmitic acid, stearic acid, behenic acid, arichidonic acid, oleic acid, isostearic acid, sebacic acid, or mixtures thereof. In some cases, the fatty acids are selected from the group consisting of palmitic acid, stearic acid, or mixtures thereof.

Fatty alcohol derivatives include alkyl ethers of fatty alcohols, alkoxylated fatty alcohols, alkyl ethers of alkoxylated fatty alcohols, esters of fatty alcohols or mixtures thereof. Nonlimiting examples of fatty alcohol derivatives include materials such as methyl stearyl ether; 2-ethylhexyl dodecyl ether; stearyl acetate; cetyl propionate; the ceteth series of compounds such as ceteth-1 through ceteth-45, which are ethylene glycol ethers of cetyl alcohol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; C1-C30 alkyl ethers of the ceteth, steareth, and ceteareth compounds just described; polyoxyethylene ethers of branched alcohols such as octyldodecyl alcohol, dodecylpentadecyl alcohol, hexyldecyl alcohol, and isostearyl alcohol; polyoxyethylene ethers of behenyl alcohol; PPG ethers such as PPG-9-steareth-3, PPG-11 stearyl ether, PPG8-ceteth-1, and PPG-10 cetyl ether; or mixtures thereof.

Non-limiting examples of polyglycerol esters of fatty acids include those of the following formula (XVII):

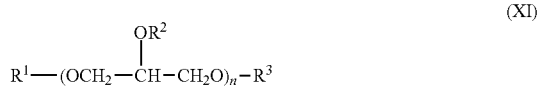

(XI)

wherein:
the average value of n is about 3; and
$R^1$, $R^2$, and $R^3$, which may be identical or different, are independently chosen from a fatty acid moiety or hydrogen, provided that at least one of $R^1$, $R^2$, and $R^3$ is a fatty acid moiety.

For instance, $R^1$, $R^2$ and $R^3$ may be saturated or unsaturated, straight or branched, and have a length of $C_1$-$C_{40}$, $C_1$-$C_{30}$, $C_1$-$C_{25}$, $C_1$-$C_{20}$, $C_1$-$C_{16}$, or $C_1$-$C_{10}$. Additionally, non-limiting examples of nonionic polyglycerol esters of fatty acids include polyglyceryl-4 caprylate/caprate, polyglyceryl-10 caprylate/caprate, polyglyceryl-4 caprate, polyglyceryl-10 caprate, polyglyceryl-4 laurate, polyglyceryl-5 laurate, polyglyceryl-6 laurate, polyglyceryl-10 laurate, polyglyceryl-10 cocoate, polyglyceryl-10 myristate, polyglyceryl-10 oleate, polyglyceryl-10 stearate, or mixtures thereof.

The fatty acid derivatives are defined herein to include fatty acid esters of the fatty alcohols as defined above, fatty acid esters of the fatty alcohol derivatives as defined above when such fatty alcohol derivatives have an esterifiable hydroxyl group, fatty acid esters of alcohols other than the fatty alcohols and the fatty alcohol derivatives described above, hydroxy-substituted fatty acids, or mixtures thereof. Nonlimiting examples of fatty acid derivatives include ricinoleic acid, glycerol monostearate, 12-hydroxy stearic acid, ethyl stearate, cetyl stearate, cetyl palmitate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, dimethyl sebacate, PEG-15 cocoate, PPG-15 stearate, glyceryl monostearate, glyceryl distearate, glyceryl tristearate, PEG-8 laurate, PPG-2 isostearate, PPG-9 laurate, or mixtures thereof. Preferred for use herein are glycerol monostearate, 12-hydroxy stearic acid, or mixtures thereof.

In some cases, the one or more fatty compounds may be one or more high melting point fatty compounds. A high melting point fatty compound is a fatty compound having a melting point of 25° C. Even higher melting point fatty compounds may also be used, for example, fatty compounds having a melting point of 40° C. or higher, 45° C. or higher, or 50° C. or higher. The high melting point fatty compound may be selected from fatty acids, fatty alcohol derivatives, fatty acid derivatives, or mixtures thereof. Nonlimiting examples of the high melting point compounds are found in the International Cosmetic Ingredient Dictionary, Sixteenth Edition, 2016, which is incorporated by reference herein in its entirety.

In some embodiments, the non-silicone fatty compounds include one or more non-silicone oils. The term "oil" as used herein describes any material which is substantially insoluble in water. Suitable non-silicone oils include, but are not limited to, natural oils, such as coconut oil; hydrocarbons, such as mineral oil and hydrogenated polyisobutene; fatty alcohols, such as octyldodecanol; esters, such as $C_{12}$-$C_{15}$ alkyl benzoate; diesters, such as propylene dipelarganate; and triesters, such as glyceryl trioctanoate. Suitable low viscosity oils have a viscosity of 5-100 mPas at 25° C., and are generally esters having the structure RCO—OR' wherein RCO represents the carboxylic acid radical and wherein OR' is an alcohol residue. Examples of these low viscosity oils include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, or combinations of octyldodecanol, acetylated lanolin alcohol, cetyl acetate, isodoecanol, polyglyceryl-3-diisostearate, or combinations thereof. The high viscosity oils generally have a viscosity of 200-1,000,000, or 100,000-250,000, mPas at 25° C. Such oils include castor oil, lanolin and lanolin derivatives, triisocetyl citrate, sorbitan sesquioleate, $C_{10}$-$C_{18}$ triglycerides, caprylic/capric/triglycerides, coconut oil, corn oil, cottonseed oil, glyceryl triacetyl hydroxystearate, glyceryl triacetyl ricinoleate, glyceryl trioctanoate, hydrogenated castor oil, linseed oil, mink oil, olive oil, palm oil, illipe butter, rapeseed oil, soybean oil, sunflower seed oil, tallow, tricaprin, trihydroxystearin, triisostearin, trilaurin, trilinolein, trimyristin, triolein, tripalmitin, tristearin, walnut oil, wheat germ oil, cholesterol, or combinations thereof.

Polymers

In accordance with the disclosure, the hair care composition may include in the various embodiments at least one polymer.

In some particular embodiments, the at least one polymer comprises hydroxyethylcellulose, modified potato starch, the anionic polymer polyacrylamide (and) C13-14 isoparaffin (and) laureth-7, hydrogenated polyisobutene, PEG-120 methyl glucose trioleate, and combinations thereof.

In accordance with the various embodiments, when present, the amount of each of the at least one styling polymer is from about 0.1% to about 10%, or from about 0.1% to about 8%, or from about 0.2% to about 7%, or from about 1% to about 5%, or from about 1.5% to about 3% or any suitable combination, sub-combination, range, or sub-range thereof by weight, based on the weight of the composition. One of ordinary skill in the art, however, will appreciate that other ranges are within the scope of the invention.

In accordance with the various embodiments, the total amount of styling polymer present in the compositions can range from about 0.1% to about 15%, or from about 0.5% to about 12%, or from about 1% to about 10%, or from about 1.5% to about 5% or any suitable combination, sub-combination, range, or sub-range thereof by weight, based on the weight of the composition. One of ordinary skill in the art, however, will appreciate that other ranges are within the scope of the invention.

Thus, any one of the at least one styling polymer is present, by weight, based on the total weight of the composition, from about 0.1, 0.2, 0.3, 0.4, 0.5, 0.6, 0.7, 0.8, 0.9, 1, 2, 3, 4, 5, 6, 7, 8, 9, to about 10 weight percent, including increments and ranges therein and there between.

Non-limiting examples of suitable polymers include anionic associative polymers, amphoteric associative polymers, nonionic associative polymers, and a mixture thereof. A non-limiting example of an amphoteric associative polymer is acrylates/beheneth-25methacrylate copolymer, sold under the tradename NOVETH IX L-10 (Lubrizol). Non-limiting examples of anionic associative polymers include INCI name: acrylates copolymer, sold under the tradename CARBOPOL Aqua SF-1 (Lubrizol), INCI name: acrylates crosspolymer-4, sold under the tradename CARBOPOL Aqua SF-2 (Lubrizol), and a mixture thereof.

Silicones

The hair treatment composition of the instant disclosure may optionally include one or more silicones. Nonetheless, in some instances the composition is free or essentially free of silicones. In other words, one or more of the following silicones may be optionally included or optionally excluded from the composition.

In some particular embodiments, the one or more silicone compound comprises one or more silicone compounds comprising phenyl trimethicone, dimethicone, and dimethicone (and) dimethiconol, and combinations of these.

In accordance with the various embodiments, when present, the amount of each of the one or more silicone compounds is from about 0.1% to about 20%, or from about 0.2% to about 15%, or from about 1% to about 10%, or from about 1.5% to about 5% or any suitable combination, sub-combination, range, or sub-range thereof by weight, based on the weight of the composition. One of ordinary skill in the art, however, will appreciate that other ranges are within the scope of the invention.

In accordance with the various embodiments, the total amount of silicone compounds present in the compositions can range from about 0.1% to about 30%, or from about 0.5% to about 20%, or from about 1% to about 15%, or from about 1.5% to about 10% or any suitable combination, sub-combination, range, or sub-range thereof by weight, based on the weight of the composition. One of ordinary skill in the art, however, will appreciate that other ranges are within the scope of the invention.

Thus, any one of the one more silicone compounds is present, by weight, based on the total weight of the composition, from about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19 to about 20 weight percent, including increments and ranges therein and there between.

More generally, suitable silicones include, but are not limited to, polyorganosiloxanes, polyalkylsiloxanes, polyarylsiloxanes, polyalkarylsiloxanes, polyestersiloxanes, or mixtures thereof. Non-limiting examples include dimethicone, cyclomethicone (cyclopentasiloxane), amodimethicone, trimethyl silyl amodimethicone, phenyl trimethicone, trimethyl siloxy silicate, polymethylsilsesquioxane or mixtures thereof.

In some instances, the compositions include (or exclude) one or more silicones selected from the group consisting of polydimethylsiloxanes (dimethicones), polydiethylsiloxanes, polydimethyl siloxanes having terminal hydroxyl groups (dimethiconols), polymethylphenylsiloxanes, phenylmethylsiloxanes, amino functional polydimethylsiloxane (amodimethicone), non-ionic dimethicone copolyols, dimethicone copolyol esters, dimethicone copolyol quaternium nitrogen containing compounds, dimethicone copolyol phosphate esters, or mixtures thereof.

The hair treatment composition may include (or exclude) one or more silicone oils, for example one or more non-phenyl silicone oils and/or one or more phenyl silicone oils. The silicone oil is, in some embodiments, apolar. An "apolar silicone oil" is intended to denote a silicon oil that does not comprise any ionic or ionisable group(s), and, in some embodiments, does not comprise any oxyalkylenated ($C_2$-$C_4$) unit(s), (in some embodiments, oxyethylene, oxypropylene), or glycerol unit(s).

Representative examples of non-volatile non-phenyl silicone oils which may be mentioned include polydimethylsiloxanes; alkyl dimethicones; vinylmethyl methicones; and also silicones modified with aliphatic groups and/or with functional groups such as hydroxyl, thiol and/or amine groups. It should be noted that "dimethicone" (INCI name) corresponds to a poly(dimethylsiloxane) (chemical name), which is particularly preferred in some instances.

The non-volatile non-phenyl silicone oil is, in some embodiments, chosen from non-volatile dimethicone oils. In particular, these oils can be chosen from the following non-volatile oils:

polydimethylsiloxanes (PDMSs);

PDMSs comprising aliphatic groups, in particular alkyl or alkoxy groups, which are pendent and/or at the end of the silicone chain, these groups each comprising from 2 to 24 carbon atoms. By way of example, mention may be made of the cetyl dimethicone sold under the commercial reference ABIL WAX 9801 from Evonik Goldschmidt;

PDMSs comprising aliphatic groups, or functional groups such as hydroxyl, thiol and/or amine groups;

polyalkylmethylsiloxanes substituted with functional groups such as hydroxyl, thiol and/or amine groups; and polysiloxanes modified with fatty acids, fatty alcohols or polyoxyalkylenes, or mixtures thereof.

In some embodiments, non-volatile, non-phenyl silicone oils are chosen from polydimethylsiloxanes, alkyl dimethicones, and also PDMSs comprising aliphatic groups, in particular $C_2$-$C_{24}$ alkyl groups, and/or functional groups such as hydroxyl, thiol, and/or amine groups.

The non-phenyl silicone oil may be chosen in particular from silicones of the following formula:

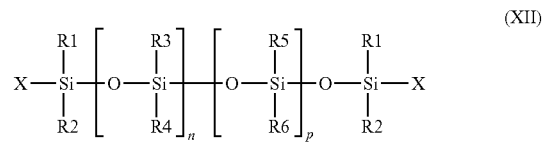

(XII)

wherein:

$R_1$, $R_2$, $R_5$, and $R_6$, which may be identical or different, are independently chosen from alkyl radicals containing 1 to 6 carbon atoms, $R_3$ and $R_4$, which may be identical or different, are independently chosen from alkyl radicals containing from 1 to 6 carbon atoms, a vinyl radical, an amine radical, or a hydroxyl radical, X is an alkyl radical containing from 1 to 6 carbon atoms, a hydroxyl radical, or an amine radical, and n and p are integers chosen so as to have a fluid compound, in particular of which the viscosity at 25° C. is between 9 centistokes (cSt) and 800 000 (cSt).

As non-volatile, non-phenyl silicone oils which can be used according to the invention, mention may be made of those for which:

the substituents $R_1$ to $R_6$ and X represent a methyl group, and p and n are such that the viscosity is 500 000 cSt, for example the product sold under the name SE30 by the company General Electric, the product sold under the name AK 500000 by the company Wacker, the product sold under the name Mirasil DM 500 000 by the company Bluestar, and the product sold under the name Dow Corning 200 Fluid 500 000 cSt by the company Dow Corning, the substituents $R_1$ to $R_6$ and X represent a methyl group, and p and n are such that the viscosity is 60 000 cSt, for example the product sold under the name Dow Corning 200 Fluid 60 000 CS by the company Dow Corning, and the product sold under the name Wacker Belsil DM 60 000 by the company Wacker, the substituents $R_1$ to $R_6$ and X represent a methyl group, and p and n are such that the viscosity is 100 cSt or 350 cSt, for example the products sold respectively under the names Belsil DM100 and Dow Corning 200 Fluid 350 CS by the company Dow Corning, the substituents $R_1$ to $R_6$ represent a methyl group, the group X represents a hydroxyl group, and n and p are such that the viscosity is 700 cSt, for example the product sold under the name Baysilone Fluid T0.7 by the company Momentive.

Additional Ingredients

In accordance with the disclosure, the hair care composition may include in the various embodiments at least one additional miscellaneous ingredient or additives such as other conditioning agents, anionic, nonionic or amphoteric agents, humectants, preservatives, chelating agents, UV filters, pH adjusters, fragrance, pigments, colorants, anti-dandruff, seborrheic agents and other skin actives.

In some particular embodiments, the composition may include one or more components comprising potassium hydroxide; sodium hydroxide; acetamide mea; lactic acid; taurine; citric acid; gluconolactone; fragrance; one or more preservatives comprising chlorhexidine dihydrochloride, phenoxyethanol, benzoic acid; and combinations of these. In some particular embodiments, the composition may include one or more emulsifiers, for example, octyldodecanol (and) octyldodecyl xyloside In accordance with the various embodiments, when present, an additive is from about 0.1% to about 10%, or from about 0.1% to about 8%, or from about 0.2% to about 7%, or from about 1% to about 5%, or from about 1.5% to about 3% or any suitable combination, sub-combination, range, or sub-range thereof by weight, based on the weight of the composition. One of ordinary skill in the art, however, will appreciate that other ranges are within the scope of the invention.

In accordance with the various embodiments, when present, the total amount of additive present in the compositions can range from about 0.1% to about 15%, or from about 0.5% to about 12%, or from about 1% to about 10%, or from about 1.5% to about 5% or any suitable combination, sub-combination, range, or sub-range thereof by weight, based on the weight of the composition. One of ordinary skill in the art, however, will appreciate that other ranges are within the scope of the invention.

Thus, when present, an additive is present, by weight, based on the total weight of the composition, from about 0.5, 0.6, 0.7, 0.8, 0.9, 1, 2, 3, 4, 5, 6, 7, 8, 9, 10, 11, 12, 13, 14, 15, 16, 17, 18, 19, to about 20 weight percent, including increments and ranges therein and there between.

In some particular embodiments, the composition includes one or more preservatives. Suitable preservatives include, but are not limited to, glycerin containing compounds (e.g., glycerin or ethylhexylglycerin or phenoxyethanol), benzyl alcohol, parabens (methylparaben, ethylparaben, propylparaben, butylparaben, isobutylparaben, etc.), sodium benzoate, benzoic acid, chlorhexidine digluconate, ethylenediamine-tetraacetic acid (EDTA), potassium sorbate, and/or grapefruit seed extract, or a mixture thereof. Other preservatives are known in the cosmetics industries and include salicylic acid, DMDM Hydantoin, Formaldahyde, Chlorphenism, Triclosan, Imidazolidinyl Urea, Diazolidinyl Urea, Sorbic Acid, Methylisothiazolinone, Sodium Dehydroacetate, Dehydroacetic Acid, Quaternium-15, Stearalkonium Chloride, Zinc Pyrithione, Sodium Metabisulfite, 2-Bromo-2-Nitropropane, Chlorhexidine Digluconate, Polyaminopropyl biguanide, Benzalkonium Chloride, Sodium Sulfite, Sodium Salicylate, Citric Acid, Neem Oil, Essential Oils (various), Lactic Acid, Vitamin E (tocopherol), and a mixture thereof. In some cases, the hair care compositions may include one or more preservatives selected from the group consisting of sodium benzoate, benzoic acid, chlorhexidine digluconate, chlorhexidine dihydrochloride, salicylic acid, phenoxyethanol, methyl paraben, and a mixture thereof.

In accordance with the various embodiments, when present, an additive in the form of one or more preservative is from about 0.1% to about 5%, or from about 0.2% to about 5%, or from about 0.3% to about 5%, or from about 1.5% to about 3% or any suitable combination, sub-combination, range, or sub-range thereof by weight, based on the weight of the composition. One of ordinary skill in the art, however, will appreciate that other ranges are within the scope of the invention.

Compositions, Methods of Use and Application, and Kits

The compositions described throughout the instant disclosure may be in a variety of different forms, including but not limited to gels, lotions, creams, emulsions, pastes, milks, sprays, serums, and the like. The compositions may be rinse-off or leave-in treatments.

In various embodiments, the composition is in the form of an aqueous solution. In an embodiment, the composition is in the form of an emulsion, such as a water-in-oil (W/O) emulsion. In one embodiment, the composition is a conditioner in the form of an W/O emulsion. In an embodiment, the compositions may be in the form of a dispersion. In an embodiment, the composition is a rinse-off treatment for conditioning and/or styling and/or shaping hair.

Additionally, when used on hair, the compositions may provide one or more desirable cosmetic and/or styling benefits to the hair, for example, smoothness, detangling, and shine. Accordingly, the compositions are useful in methods for conditioning hair, and methods for imparting frizz control, manageability, smoothness, detangling, and/or shine to hair. Accordingly, the instant disclosure encompasses methods for treating hair with the compositions of the instant disclosure. Such methods may include simply applying a composition of the instant disclosure to the hair, and optionally rinsing the hair.

In some cases, methods of using the compositions include shampooing and/or conditioning the hair with a composition of the instant disclosure. Such methods typically include applying an effective amount of a hair treatment composition of the instant disclosure to the hair, allowing the composition to remain on the hair for a period of time, and subsequently optionally rinsing the composition from the hair. The period of time for which the composition is allowed to remain on the hair is usually not long, e.g., not longer than about 5 minutes. Usually, the composition is merely allowed to remain on the hair for a period of time sufficient to incorporate the composition throughout the hair, for example, by lathering or spreading the composition throughout the hair using one's hands. The amount of time is sufficient for the composition to interact with the hair and any dirt, oil, contamination, etc., that may exist on the hair so that when rinsed, the agents of the composition can interact with the hair to condition it and confer styling benefits. Thus, the composition may be allowed to remain on the hair for about 5 seconds to about 30 minutes, about 5 seconds to about 15 minutes, about 5 seconds to about 10 minutes, about 5 seconds to about 5 minutes, about 10 seconds to about 5 minutes, or about 10 seconds to about 3 minutes.

As is common when using shampoo and/or conditioner and/or masque compositions, the hair may be wetted or rinsed with water prior to application of the hair treatment composition of the instant disclosure. Having water already in the hair can be helpful, e.g. for creating lather when applying compositions such as shampoos because the water interacts with the surfactants of the shampoo's surfactant system.

Typically, a shampoo and a conditioner are used in a hair care routine in the form of a bundle system in order to cleanse then condition the hair. Optionally, another composition, e.g. a masque, may be used after a conditioner in order to impart deeper conditioning to the hair or to deliver other active or benefit agents such as styling agent to the hair. Optionally, a pre-shampoo treatment composition may also be applied onto hair before shampooing in order to deliver additional benefits to the hair. Optionally, an in-shower treatment composition may be mixed, in situ on hair or before treating hair, with a shampoo and/or conditioner in order to enhance the cleansing and/or conditioning of the hair. As such, it is possible to have kits comprising one, two, three, or more of these compositions, each composition packaged separately. Any known means of packaging the compositions separately in a kit may be used, e.g. separate bottles or containers for each composition, a single bottle with separate compartments for each composition, etc.

Implementation of the present disclosure is provided by way of the following Examples. The Examples serve to illustrate the technology, without being limiting in nature.

EXAMPLES

The following Examples are intended to be non-restrictive and explanatory only. The ingredient amounts in the compositions/formulas described below are expressed in % by weight, based on the total weight of the composition.

Several formulas were produced, in some specific examples having ingredients that include those listed in the tables below. Not all components of the compositions are listed in the representative components Table 2, below. Table 2 lists raw materials, and the subsequent tables list amounts of actives, with the understanding that not all actives are present at 100% in the raw materials. The balance of all formulas was water.

Example I: Key Raw Materials

TABLE 2

Representative Components

| Component | Ingredient | Trade Name, Supplier and Concentration |
|---|---|---|
| Polysaccharide | Inulin | Supplied by Creachem |
| Film-forming aminosilicone polymer that is the product of reaction between an oxirane or oxetane | PolySilicone-29 | Supplied by Momentive |

TABLE 2-continued

Representative Components

| Component | Ingredient | Trade Name, Supplier and Concentration |
|---|---|---|
| compound comprising at least two oxirane or oxetane groups and an amino silane | | |

Example 2: Inventive Compositions

TABLE 3

Inventive Compositions 1-3

| INGREDIENTS, US INCI NAME | INV 1 Water-in-oil emulsion | INV 2 aqueous | INV 3 aqueous |
|---|---|---|---|
| C13-14 ISOPARAFFIN | 0.42 | 0.84 | 0.315 |
| SILICONES: DIMETHICONE AND/OR DIMETHICONOL | | | 17 |
| FRAGRANCE | | | 0.6 |
| HYDROGENATED POLYISOBUTENE | 3.9998 | | |
| INULIN | 0.97 | 0.97 | 0.97 |
| LAURETH-7 | 0.14 | 0.28 | 0.105 |
| MINERAL OIL | 5 | | |
| OCTYLDODECANOL | 1.2 | | |
| OCTYLDODECYL XYLOSIDE | 0.4 | | |
| PEG-120 METHYL GLUCOSE TRIOLEATE | | 1.6 | |
| PEG-30 DIPOLYHYDROXYSTEARATE | 0.4 | | |
| PEG-40 HYDROGENATED CASTOR OIL | | | 1 |
| PHENYL TRIMETHICONE | | | 2 |
| POLYACRYLAMIDE | 0.8 | 1.6 | 0.6 |
| POLYSILICONE-29 | 0.15 | 0.15 | 0.15 |
| PROPYLENE GLYCOL | | 1.6 | 40 |
| SODIUM COCOAMPHOPROPIONATE | | 12 | |
| ORGANIC SOLVENTS: DIPROPYLENE GLYCOL AND/OR HEXYLENE GLYCOL | 0.5 | 0.5 | 8.5 |
| ADDITIVES: ONE OR MORE OF PRESERVATIVES, PH ADJUSTER, NEUTRALIZERS, VITAMINS, FRAGANCE: ETHYLHEXYLGLYCERIN, SODIUM BENZOATE, PHENOXYETHANOL | <2 | <2 | <2 |
| WATER | Q.S. 100 | Q.S. 100 | Q.S. 100 |

TABLE 4

Inventive Composition 4

| INGREDIENTS | INV 4 Cream gel |
|---|---|
| PHENYL TRIMETHICONE | 2 |
| POLYSILICONE-29 | 0.15 |
| HYDROXYPROPYL GUAR | 0.5 |
| SILICONES: DIMETHICONE AND/OR DIMETHICONOL | 17.0 |
| ORGANIC SOLVENT: DIPROPYLENE GLYCOL AND/OR ALCOHOL DENAT. | 0.6 |
| WATER | Q.S. 100 |
| HYDROXYETHYLCELLULOSE | 0.5 |
| INULIN | 0.97 |

TABLE 4-continued

Inventive Composition 4

| INGREDIENTS | INV 4 Cream gel |
|---|---|
| POTATO STARCH MODIFIED | 0.4988 |
| ADDITIVES: ONE OR MORE OF PRESERVATIVES, PH ADJUSTER, NEUTRALIZERS, VITAMINS, FRAGANCE: ETHYLHEXYLGLYCERIN, SODIUM BENZOATE, PHENOXYETHANOL | <2 |

Example 3: Comparative Composition

TABLE 5

Commercial Shampoo

| INGREDIENT INCI US | COMP SHAMPOO |
|---|---|
| AMODIMETHICONE | 0.6 |
| LAURETH-5 CARBOXYLIC ACID | 0.72 |
| HEXYLENE GLYCOL | 0.5 |
| POLYQUATERNIUM-7 | 0.495 |
| SODIUM LAURETH SULFATE | 8.05 |
| PROPYLENE GLYCOL | 0.24 |
| PEG-60 HYDROGENATED CASTOR OIL | 0.15 |
| COCAMIDE MIPA | 0.7 |
| COCO-BETAINE | 4.5 |
| WATER | Q.S. 100 |
| PEG-55 PROPYLENE GLYCOL OLEATE | 0.24 |
| PLANT EXTRACTS AND PLANT OILS | <0.5 |
| ADDITIVES: PRESERVATIVES, VITAMINS, PH ADJUSTER, NEUTRALIZERS, COLORANTS, SODIUM CHLORIDE | <5.0 |

Example 3: Comparative Composition

TABLE 6

COMMERCIAL CONDITIONER

| INGREDIENT INCI US | COMP CONDITIONER |
|---|---|
| TRIDECETH-6 | 0.15 |
| CETRIMONIUM CHLORIDE | 0.03 |
| ISOPROPYL ALCOHOL | 0.576 |
| CETEARYL ALCOHOL | 6.5 |
| AMODIMETHICONE | 1.71 |
| WATER | Q.S. 100 |
| PLANT EXTRACTS AND PLANT OILS | <0.5 |
| ADDITIVES: PRESERVATIVES, VITAMINS, PH ADJUSTER, NEUTRALIZERS, COLORANTS | <5.0 |

Example 4: Expert Testing

A cohort of 5 subjects, each having medium to long hair, with average to course hair texture, and a straight to wavy hair recruited into a study. Each subject's hair was treated with Comparative Shampoo on the full head of hair; thereafter, half of the head of hair for each subject was treated with Comparative Conditioner, and half of the head of hair for each subject received Inventive Conditioner 4, which is a composition according to the disclosure that includes a novel association of polysaccharide, for example, Inulin, and a film-forming polymer, for example polysilicone-29, hydroxypropyl guar, hydroxyethylcellulose, and potato starch modified, and including silicones and styling polymers. After rinsing to remove the applied conditioner to the test half of each subject's hair, the hair was blow-dried to style.

Referring now to Table 7, below, the expert evaluator reported on the performance of the control and test subject hair with respect to a set of performance features.

TABLE 7

| PERFORMANCE FEATURE | EXPERT GRADE (INV vs COMP) |
|---|---|
| Easy combing | ≥ |
| Easy Blow-dry | ≥ |
| Fast Blow-dry | > |
| Discipline | ≥ |
| Frizz Amount | = |
| Smooth Look & Feel | >, < wet feel |
| Shape Control | − |
| Shine | ≥ |
| Clean Feel | ≥ |
| Product Texture & Aspect | < |
| Usage Qualities | < |

The foregoing description illustrates and describes the invention. The disclosure shows and describes only the preferred embodiments but it should be understood that the invention is capable to use in various other combinations, modifications, and environments and is capable of changes or modifications within the scope of the inventive concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein.

As used herein, the terms "comprising," "having," and "including" (or "comprise," "have," and "include") are used in their open, non-limiting sense. The phrase "consisting essentially of" limits the scope of a claim to the specified materials or steps and those that do not materially affect the basic and novel characteristics of the claimed invention.

The terms "a," "an," and "the" are understood to encompass the plural as well as the singular.

Thus, the term "a mixture thereof" also relates to "mixtures thereof." Throughout the disclosure, if the term "a mixture thereof" is used, following a list of elements as shown in the following example where letters A-F represent the elements: "one or more elements selected from the group consisting of A, B, C, D, E, F, or mixtures thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, or mixtures thereof," it indicates that that one or more of A, B, C, D, and F may be included, one or more of a salt of A, a salt of B, a salt of C, a salt of D, a salt of E, and a salt of F may be include, or a mixture of any two of A, B, C, D, E, F, a salt of A, a salt of B, a salt of C, a salt of D, a salt of E, and a salt of F may be included.

The salts referred to throughout the disclosure may include salts having a counter-ion such as an alkali metal, alkaline earth metal, or ammonium counterion. This list of counterions, however, is non-limiting.

The expression "one or more" means "at least one" and thus includes individual components as well as mixtures/combinations.

The term "plurality" means "more than one" or "two or more."

Other than in the operating examples, or where otherwise indicated, all numbers expressing quantities of ingredients and/or reaction conditions can be modified in all instances by the term "about," meaning within +/−1%, 2%, 3%, 4%, or 5% of the indicated number.

Some of the various categories of components identified for the hair care compositions may overlap. In such cases where overlap may exist and the composition/product includes two overlapping components (or more than two overlapping components), an overlapping component does not represent more than one component. For example, a fatty acid may be defined as both a "fatty compound" and a "surfactant/emulsifier." If a particular composition/product includes both a fatty compound component and an emulsifier component, a single fatty acid can serve as only a fatty compound or a surfactant/emulsifier (a single fatty acid does not serve as both the fatty compound and the surfactant/emulsifier).

All percentages, parts and ratios herein are based upon the total weight of the compositions of the present invention, unless otherwise indicated.

All ranges and values disclosed herein are inclusive and combinable. For examples, any value or point described herein that falls within a range described herein can serve as a minimum or maximum value to derive a sub-range, etc. Furthermore, all ranges provided are meant to include every specific range within, and combination of sub-ranges between, the given ranges. Thus, a range from 1-5, includes specifically points 1, 2, 3, 4 and 5, as well as sub-ranges such as 2-5, 3-5, 2-3, 2-4, 1-4, etc.; and points of 1, 2, 3, 4, and 5 includes ranges and sub-ranges of 1-5, 2-5, 3-5, 2-3, 2-4, 1-4, etc.

All numbers herein are understood to be modified by "about," whether or not expressly stated. Additionally, all numbers are intended to represent exact figures as additional embodiments, whether or not modified by "about." For example, "an amount of about 1%" includes an amount of exactly 1%. As a further example, "an amount of 1%" includes an amount of about 1%. The term "about" is generally understood to encompass a range of +/−10% from the stated number, and is intended to cover amounts of +/−1%, 2%, 3%, 4%, 5%, 6%, 7%, 8%, 9%, and 10%.

The term "surfactants" includes salts of the surfactants even if not explicitly stated. In other words, whenever the disclosure refers to a surfactant, it is intended that salts of the surfactant are also encompassed to the extent such salts exist, even though the specification may not specifically refer to a salt (or may not refer to a salt in every instance throughout the disclosure), for example, by using language such as "a salt thereof" or "salts thereof." Sodium and potassium are common cations that form salts with surfactants. However, additional cations such as ammonium ions, or alkanolammonium ions such as monoethanolammonium or triethanolammonium ions, may also form salts of surfactants.

The term "substantially free" or "essentially free" as used herein means the specific material may be present in small amounts that do not materially affect the basic and novel characteristics of the claimed invention. For instance, there may be less than 1% by weight of a specific material added to a composition, based on the total weight of the compositions (provided that an amount of less than 1% by weight does not materially affect the basic and novel characteristics of the claimed invention. Similarly, the compositions may include less than 0.5 wt %, less than 0.1 wt %, less than 0.05 wt %, or less than 0.01 wt %, or none of the specified material. Furthermore, all components that are positively set forth in the instant disclosure may be negatively excluded from the claims, e.g., a claimed composition may be "free," "essentially free" (or "substantially free") of one or more components that are positively set forth in the instant disclosure.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A hair care composition, comprising:
   a. at least one polysaccharide;
   b. polysilicone-29;
   c. water; and
   d. two or more of:
      i. at least one polymer comprising one or more of polyacrylamide, hydroxypropyl guar, hydroxyethylcellulose, modified potato starch, or combinations thereof, wherein each of the at least one polymer, if present, is present from about 0.1% to about 20% by weight of the composition;
      ii. at least one amphoteric surfactant comprising one or more of betaines, alkyl sultaines, alkyl amphoacetates, alkyl amphoprionates, salts thereof, or combinations thereof, wherein each of the at least one amphoteric surfactant, if present, is present from about 0.1% to about 20% by weight of the composition; or
      iii. at least one silicone compound comprising one or more of phenyl trimethicone, dimethicone, dimethicone (and) dimethiconol, or combinations thereof, wherein each of the at least one silicone compound, if present, is present from about 0.1% to about 20% by weight of the composition,
   wherein the hair care composition is free of cationic polymers.

2. The hair care composition according to claim 1, wherein the at least one polysaccharide is a plant gum selected from inulin, carrageenan, pullulan and combinations thereof.

3. The hair care composition according to claim 1, wherein the at least one polysaccharide is present in an amount from about 0.2% to about 10% by weight of the composition, and the polysilicone-29 is present in an amount from about 0.5% to about 20% by weight of the composition.

4. The hair care composition according to claim 1, comprising a cosmetically acceptable carrier comprising:
   the water which is present in an amount that is at least 20% by weight of the composition; and
   one or more water-soluble solvents.

5. The hair care composition according to claim 4, wherein the one or more water-soluble solvents comprises polyols.

6. The hair care composition according to claim 1, comprising a cosmetically acceptable carrier comprising:
the water which is present in an amount that is at least 70% by weight of the composition; and
one or more water-soluble solvents comprising polyols.

7. The hair care composition according to claim 1, comprising at least one fatty compound present from about 0.1% to about 10% by weight of the composition.

8. The hair care composition according to claim 1, the composition comprising the at least one polymer and further comprising the emulsifier octyldodecanol and octyldodecyl xyloside.

9. The hair care composition according to claim 8, wherein the at least one polymer comprises the polyacrylamide.

10. The hair care composition according to claim 9, further comprising at least one surfactant comprising one or more non-ionic surfactants that include PEG-30 dipolyhydroxystearate.

11. The hair care composition according to claim 1, wherein the composition comprises the at least one amphoteric surfactant and the at least one polymer.

12. The hair care composition according to claim 1, wherein the composition comprises the at least one polymer and further comprises one or more water-soluble solvents comprising polyols present in an amount of at least 40% by weight.

13. The hair care composition according to claim 12, wherein the at least one polymer comprises the polyacrylamide.

14. The hair care composition according to claim 13, further comprising one or more non-ionic surfactants and the at least one silicone compound.

15. The hair care composition according to claim 1, wherein the composition comprises the at least one polymer selected from the hydroxypropyl guar, the hydroxyethylcellulose, the modified potato starch, or combinations thereof, and the at least one silicon compound comprising one or more of the phenyl trimethicone, the dimethicone, or the dimethicone and dimethiconol.

16. The hair care composition according to claim 1, wherein the hair care composition includes the polyacrylamide and further includes C13-14 isoparaffin and laureth-7.

17. A hair care composition, comprising:
a. polysaccharides chosen from inulin, carrageenan, pullulan, and combinations thereof;
b. polysilicone-29;
c. water present in an amount that is at least 20% by weight of the composition;
d. polyacrylamide;
e. C13-14 isoparaffin; and
f laureth-7,
wherein the hair care composition is free of cationic polymers.

18. The hair care composition according to claim 17, wherein the composition further comprises one or more of at least one fatty compound, at least one silicone, at least one nonionic surfactant, at least one water-soluble solvent comprising polyols, at least one emulsifier, or combinations thereof.

19. The hair care composition according to claim 18, wherein the composition further comprises at least one amphoteric surfactant.

20. The hair care composition according to claim 17, wherein the composition is free of ethanol.

21. A hair care composition, comprising:
a. at least one polysaccharide;
b. polysilicone-29; and
c. water,
wherein the hair care composition is free of cationic polymers.

* * * * *